US012245892B2

(12) United States Patent
N'Djin et al.

(10) Patent No.: US 12,245,892 B2
(45) Date of Patent: Mar. 11, 2025

(54) METHOD AND APPARATUS FOR IMAGING IN REAL TIME THE PROPAGATION OF A MECHANICAL WAVE IN AN ACOUSTICALLY PROPAGATIVE MATERIAL

(71) Applicants: INSTITUT NATIONAL DE LA SANTE DE LA RECHERCHE MEDICALE (INSERM), Paris (FR); UNIVERSITÉ CLAUDE BERNARD LYON, Villeurbanne (FR); CENTRE LÉON-BÉRARD, Lyons (FR)

(72) Inventors: William Apoutou N'Djin, Lyons (FR); Kazuhiro Matsui, Tokyo (JP); Françoise Chavrier, Lyons (FR); Rémi Souchon, Lyons (FR)

(73) Assignees: INSTITUT NATIONAL DE LA SANTE DE LA RECHERCHE MEDICALE (INSERM), Paris (FR); UNIVERSITÉ CLAUDE BERNARD LYON, Villeurbanne (FR); CENTRE LÉON-BÉRARD, Lyons (FR)

( * ) Notice: Subject to any disclaimer, the term of this patent is extended or adjusted under 35 U.S.C. 154(b) by 782 days.

(21) Appl. No.: 16/476,674

(22) PCT Filed: Jan. 10, 2018

(86) PCT No.: PCT/EP2018/050588
§ 371 (c)(1),
(2) Date: Jul. 9, 2019

(87) PCT Pub. No.: WO2018/130587
PCT Pub. Date: Jul. 19, 2018

(65) Prior Publication Data
US 2019/0374205 A1 Dec. 12, 2019

(30) Foreign Application Priority Data
Jan. 11, 2017 (EP) .................................. 17305037

(51) Int. Cl.
*G01N 29/07* (2006.01)
*A61B 8/00* (2006.01)
(Continued)

(52) U.S. Cl.
CPC .......... *A61B 8/5207* (2013.01); *A61B 8/4494* (2013.01); *A61N 7/02* (2013.01);
(Continued)

(58) Field of Classification Search
CPC ......... G06K 9/623; G06K 9/6227–623; G06K 9/6271; G06V 10/235; G06V 10/40;
(Continued)

(56) References Cited

U.S. PATENT DOCUMENTS 5,558,092 A * 9/1996 Unger .................. A61B 8/0833
601/3
6,575,922 B1 6/2003 Fearnside et al.
(Continued)

FOREIGN PATENT DOCUMENTS

EP 2272434 A1 * 1/2011 ............. A61B 6/463
JP 2013 215522 A 10/2013
(Continued)

OTHER PUBLICATIONS

Frohly et al.; "Ultrasonic cavitation monitoring by acoustic noise power measurement"; Journal of the Acoustical Society of America, vol. 108, No. 5, Pt. 1, Nov. 2000, pp. 2012-2020.
(Continued)

*Primary Examiner* — Jason M Ip
(74) *Attorney, Agent, or Firm* — WC&F IP

(57) ABSTRACT

This method for imaging in real time the propagation of a mechanical wave in an acoustically propagative medium comprises steps of: a) emitting (1000) a mechanical wave in an acoustically propagative medium, using an acoustic source being placed in an emission region of the acoustically
(Continued)

propagative medium, b) measuring (1002) voltage signal waveform values at a reception region, using an acoustic measurement unit; c) calculating (1004) acoustic field values in the acoustically propagative medium, between the emission region and the reception region, using a reconstruction algorithm implemented in a signal processing unit, and the signal waveform values measured during step b) d) generating an image, using an image generation device and using the calculated acoustic field values.

20 Claims, 8 Drawing Sheets

(51) Int. Cl.
*A61N 7/02* (2006.01)
*G01N 29/28* (2006.01)
*A61N 7/00* (2006.01)

(52) U.S. Cl.
CPC ............ *G01N 29/07* (2013.01); *G01N 29/28* (2013.01); *A61N 2007/0052* (2013.01); *G01N 2291/023* (2013.01)

(58) Field of Classification Search
CPC ...... G06V 2201/03; G06V 10/82; A61B 8/14; A61B 8/4444; A61B 8/5207; A61B 8/465; A61B 8/523; A61B 8/483; A61B 6/032; A61B 6/5223; A61B 8/0866; A61B 8/5223; A61B 8/4477; A61B 8/4494; G06N 3/0454; G06N 3/08; G06T 1/00; A61N 2007/0052; G01N 29/07
See application file for complete search history.

(56) References Cited

U.S. PATENT DOCUMENTS

| | | | | |
|---|---|---|---|---|
| 8,852,103 | B2* | 10/2014 | Rothberg | ................. A61N 7/02 600/459 |
| 2005/0245824 | A1 | 11/2005 | Schafer et al. | |
| 2007/0055155 | A1* | 3/2007 | Owen | ..................... A61B 8/00 600/439 |
| 2009/0131797 | A1* | 5/2009 | Jeong | ....................... A61B 8/54 600/459 |
| 2013/0144165 | A1* | 6/2013 | Ebbini | ................ G01S 15/8927 600/439 |
| 2013/0296743 | A1* | 11/2013 | Lee | ......................... G16H 50/30 601/3 |
| 2018/0140871 | A1* | 5/2018 | Konofagou | .............. A61N 7/02 |

FOREIGN PATENT DOCUMENTS

WO 2007/022484 A2 2/2007
WO 2012/014192 A2 2/2012

OTHER PUBLICATIONS

Lakestani et al.; "Genération d'une onde ultrasohnore plane en forme d'echelon: application a l'étalonnage de récepteurs piézoeléctriques"; J. Phys. D: appl. Phys., vol. 9, 1976, pp. 547-556.

Maynard et al.; "Nearfield acoustic holography: I. Theory of generalized holography and the development of NAH"; Journal of the Acoustical Society of America, vol. 78, No. 4, Oct. 1985, pp. 1395-1413.

Hald; "Time Domain Acoustical Holography and Its Applications"; Sound and Vibration, Instrumentation Reference Issue, Feb. 2001, pp. 16-24.

Batel et al.; "Noise Source Location Techniques—Simple to Advanced Applications"; Sound and Vibration, Mar. 2003, pp. 24-36.

Zhou et al.; "Measurement of high intensity focused ultrasound fields by a fiber optic probe hydrophone"; Journal of the Acoustical Society of America, vol. 120, No. 2, Aug. 2006, pp. 1-23.

Neumann et al.; "Schlieren visualization of ultrasonic wave fields with high spatial resolution"; Ultrasonics, vol. 44, 2006, pp. e1561-e1566.

Miyasaka et al.; "Quantitative measurement of focused ultrasound pressure field by background-subtracted shadowgraph using holographic diffuser as screen"; Japanese Journal of Applied Physics, vol. 53, 07KF24, 2014, pp. 1-5.

Golay; "Complimentary Series", IRE Transactions on Information Theory, Apr. 1961, pp. 82-87.

Harris; "A Discussion of Procedures for Ultrasonic Intensity and Power Calculations from Miniature Hydrophone Measurements"; Ultrasound in Medicine and Biology, vol. 11, No. 6, 1985, pp. 803-817.

\* cited by examiner

METHOD AND APPARATUS FOR IMAGING IN REAL TIME THE PROPAGATION OF A MECHANICAL WAVE IN AN ACOUSTICALLY PROPAGATIVE MATERIAL

TECHNICAL FIELD OF THE INVENTION

The present invention relates to a method and an apparatus for imaging in real time the propagation of a mechanical wave inside an acoustically propagative medium.

BACKGROUND OF THE INVENTION

Therapeutic ultrasound methods are known, in which a beam of ultrasound waves is generated and applied to an acoustically propagative medium, such as a soft material, for example a biological tissue, in order to create thermal or mechanical lesions in specific target regions inside the medium. The lesions are used to induce a desired effect, such as damaging a defect in the medium, e.g. for removing a tumor in a biological tissue.

The clinical acceptability of these methods is however hindered by due to the lack of suitable real-time methods for imaging the propagation of ultrasound waves inside the medium.

Traditionally, the medium is imaged using known methods before applying ultrasound waves. Focusing parameters of the beam of ultrasound waves are calculated, using theoretical models and based on the acquired images, in order to focus the ultrasound beam at the desired target region. Then, the beam of ultrasound waves is applied blindly. The medium is then imaged again, in order to assess the effect generated to the medium by the beam. These steps may be repeated as often as necessary until the desired effect is obtained, for example, until the defect is successfully damaged.

However, in practice, the beam of ultrasound waves may be strongly attenuated, or may even focus outside the desired target region, for example due to uncontrollable experimental parameters, such as a bad contact at the interface between the ultrasound source and the medium, or due to the presence, inside the medium, of multiple layers having different sound transmission properties, such as muscle, skin or fat in the case of a biological tissue. These experimental parameters are difficult to quantify precisely a priori, and cannot be completely accounted for during calculation of the focusing parameters.

There is therefore a risk of applying the energy and thus creating a lesion at a wrong position inside the medium. In this case, the desired effect is not obtained, and unnecessary lesions may be created outside the target region. This is obviously an undesirable situation.

Hydrophone-based techniques are known, for imaging the propagation of ultrasound waves in water either using direct measurements, such as in Harris "A discussion of procedures for ultrasonic intensity and power calculations from miniature hydrophone measurements" Ultrasound Med Biol 1985; 11(6):803-817 or with remote measurements, such as in Maynard et al. "Nearfield acoustic holography: I. Theory of generalized holography and the development of NAH" J Acoust Soc Am 1985; 78(4):1395-1413. In order to image an entire region, a raster-scan method must be used, by repeatedly moving physically the hydrophone at many different points in space to cover an entire imaging plane, which is time consuming. In addition, direct measurements of high intensity ultrasound waves can damage the hydrophone sensor

SUMMARY OF THE INVENTION

The object of the present invention is therefore to provide a method for imaging, in real time, the propagation of a mechanical wave inside an acoustically propagative medium.

To that end, the invention relates to a method for imaging in real time the propagation of an ultrasound wave in an acoustically propagative medium, comprising steps of:
a) emitting a mechanical wave in an acoustically propagative medium, using an acoustic source being placed in an emission region of the acoustically propagative medium,
b) measuring voltage signal waveform values at a reception region, using an acoustic measurement unit, said acoustic measurement unit including a sensor array comprising an array of individual sensors arranged along an orientation axis, and being placed at the reception region, said measurement comprising the simultaneous acquisition, by at least a sub-group of the sensors of the sensor array, of voltage signal waveform values at the reception region, for successive instants in time;
c) calculating acoustic field values in the acoustically propagative medium, between the emission region and the reception region, using a reconstruction algorithm implemented in a signal processing unit, and the signal waveform values measured during step b)
d) generating an image, using an image generation device and using the calculated acoustic field values.

An advantage of the invention is that the propagation of the ultrasound wave between the emission region and the reception is imaged in real time, thanks to the fact that the acquisition is performed simultaneously by at least some of the individual sensors. The image generation device allows for a fast and accurate reconstruction of the image, allowing a real-time imaging and visualization. This method can be used reliably with ultrasound waves of high intensity that would typically damage hydrophones, and in acoustically propagative media such as soft materials, including optically opaque ones.

According to advantageous aspects, the invention comprises one or more of the following features, considered alone or according to all possible technical combinations:
During step b), the voltage signal waveform values at the reception region are acquired simultaneously for the sensors of the sensor array.
During step b), voltage signal waveform values are acquired by a predefined sub-group of sensors in response to the mechanical wave generated during step a), said predefined sub-group of sensors being chosen among several different sub-groups of sensors; and steps a) and b) are repeated for each sub-group of sensors, the acquisition being performed each time using a different sub-group of sensors and, during step c) and d), the acoustic field values are calculated from the voltage signal waveform values measured by the sub-groups of sensors and the image is generated from the calculated acoustic field values for the sub-groups of sensors.
During step b), voltage signal waveform values are acquired by a predefined sub-group of sensors in response to the mechanical wave generated during step a), said predefined sub-group of sensors being chosen among several different sub-groups of sensors; and during step c), the acoustic field values are calculated in a portion of the acoustically propagative medium, between the emission region and the reception region, using a reconstruction algorithm implemented in a signal processing unit, and the signal waveform values measured during step b) and steps a), b) and c) are repeated for each sub-group of sensors, the acquisition being performed each time using a different sub-group of sensors and during step d) the image is generated from the calculated acoustic field values for the sub-groups of sensors.

During step b), the acquisition of voltage signal waveform values by the sensors is synchronized in time with the emission of the mechanical wave by the acoustic source using a timing control unit.

The reception region is located opposite to the emission region and whereas the sensor array is facing the acoustic source, the alignment axis of sensor array thus being aligned with the emission region along the alignment axis, and in that during step c) the acoustic field values are calculated along a geometrical plane parallel to the alignment axis and to the orientation axis.

The method further comprises steps of:
  a') emitting an additional mechanical wave using transducers of the sensor array within said medium,
  b') measuring voltage signal waveform values at a reception region, using sensor array, corresponding to the superposition of mechanical waves with the reflection of the additional mechanical wave,
and steps c) and d) further comprise the generation of a background image of the acoustically propagative medium itself, and comprise the combination of said background image with the generated image of the propagation of the mechanical waves in order to generate a composite image.

At least one of ultrasound waves is generated using coded excitation.
  During step a), the generated mechanical waves are ultrasound waves, wherein the acoustic source is an ultrasound source and wherein acoustic measurement unit is an ultrasound measurement unit, said ultrasound waves being preferably generated with a wave frequency spectrum comprised between 100 kHz and 150 MHz.

According to another aspect, the invention relates to an apparatus for real-time imaging of the propagation of an ultrasound wave in an acoustically propagative medium, said apparatus comprising:
  an acoustic source,
  an acoustic measurement unit, including a sensor array comprising an array of individual pressure sensors arranged along an orientation axis, and
  a signal processing unit,
  an image generation device,
and wherein the apparatus is configured to execute steps of:
  a) emitting a mechanical wave in an acoustically propagative medium, using an acoustic source being placed in an emission region of the acoustically propagative medium,
  b) measuring voltage signal waveform at a reception region, using an acoustic measurement unit, said acoustic measurement unit including a sensor array comprising an array of individual sensors arranged along an orientation axis, and being placed at the reception region, said measurement comprising the simultaneous acquisition, by at least a sub-group of the sensors of the sensor array, of voltage signal waveform values at the reception region, for successive instants in time;
  c) calculating acoustic field values in the acoustically propagative medium, between the emission region and the reception region, using a reconstruction algorithm implemented in a signal processing unit, and the signal waveform values measured during step b)
  d) generating an image, using an image generation device and using the calculated acoustic field values.

According to advantageous aspects, the invention comprises one or more of the following features, considered alone or according to all possible technical combinations:

The apparatus comprises a timing control unit adapted to synchronize in time the acquisition of voltage signal waveform values by the sensors with the emission of the mechanical wave by the acoustic source.

During step b), the voltage signal waveform values at the reception region are acquired simultaneously for all the sensors of the sensor array.

The reception region is adapted to be located opposite to the emission region with the sensor array is facing the acoustic source, the sensor array thus being aligned with the emission region along the alignment axis, the apparatus being further configured so that during step c) the acoustic field values are calculated along a geometrical plane parallel to the alignment axis and to the orientation axis.

The measurement unit comprises a two-dimensional sensor matrix comprising several adjacent sensor arrays each comprising an array of individual sensors arranged along parallel orientation axes, and wherein the image generation device is programmed to generate a three-dimensional image of the spatial distribution of the acoustic field values in the soft material, between the emission region and the reception region, measured using the two-dimensional sensor matrix, in a volume of the acoustically propagative medium.

The generated mechanical waves are ultrasound waves, wherein the acoustic source is an ultrasound source and wherein acoustic measurement unit is an ultrasound measurement unit, said ultrasound source being preferably adapted to generate ultrasound waves with a wave frequency comprised between 100 kHz and 150 MHz.

BRIEF DESCRIPTION OF THE DRAWINGS

The invention will be better understood upon reading the following description, provided solely as an example, and made in reference to the appended drawing, in which.

DETAILED DESCRIPTION OF SOME EMBODIMENTS

Figure 1:
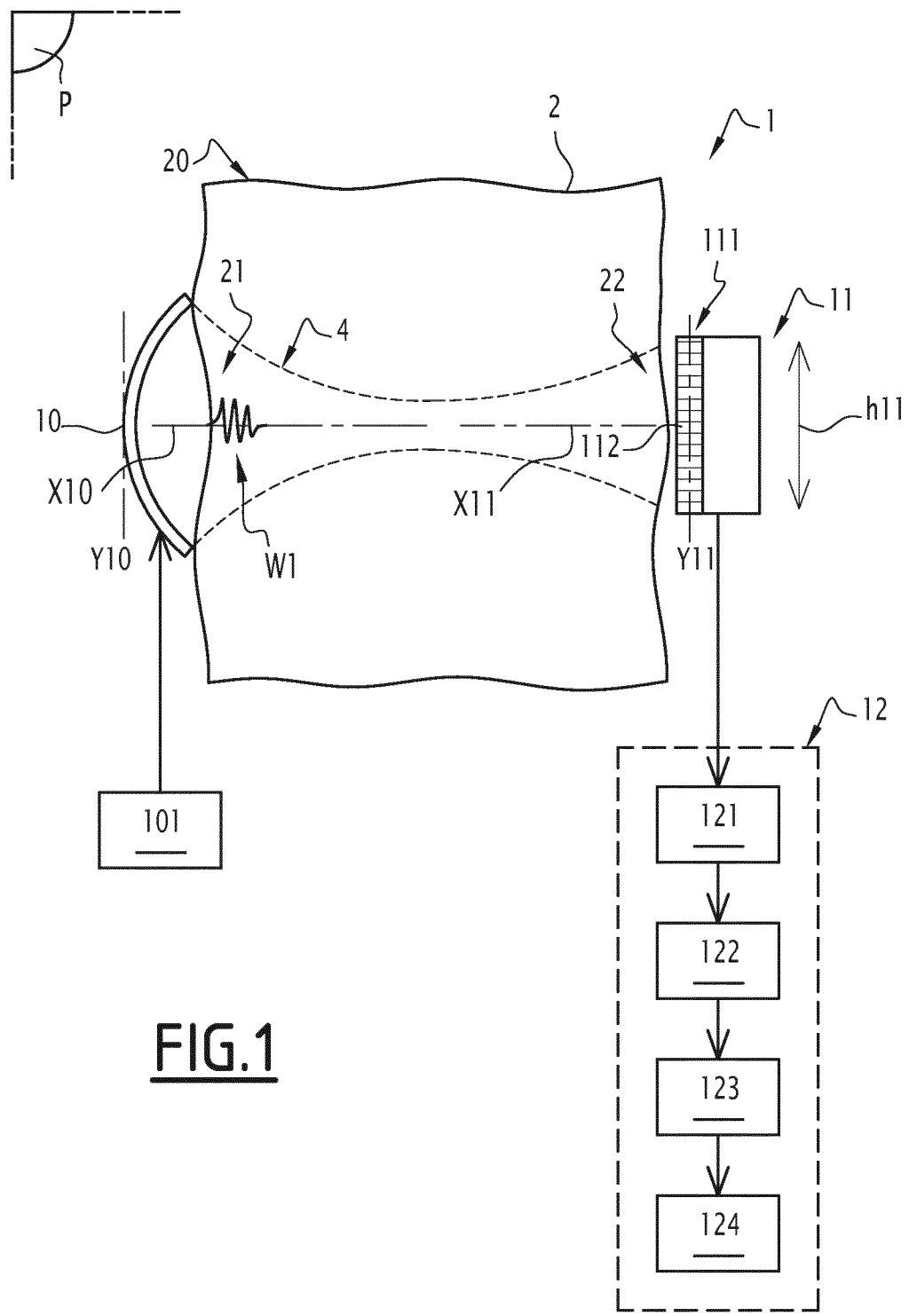
FIG. 1 is a simplified diagrammatic representation of an apparatus according to the invention for imaging in real time the propagation of a mechanical wave in an acoustically propagative medium.

FIG. 1 illustrates an apparatus 1 for imaging in real time the propagation of mechanical waves in an acoustically propagative medium 2. In the following examples, the mechanical waves are ultrasound waves.

In practice, apparatus 1 is adapted to image in real time the propagation of any ultrasound waves. In this example, apparatus 1 is described as imaging an ultrasound wave W1 composed of cycles emitted continuously.

In what follows, acoustically propagative medium 2 is a soft material, such as an organic tissue, which can be of animal or vegetal origin. For instance, soft material 2 can be an organ of a human body, of an animal body. Acoustically propagative medium 2 can also be a gel, a fluid or a liquid such as water, or a natural or synthetic material.

In this illustrative example, medium 2 comprises an outer envelope 20, which surrounds medium 2 and serves as a boundary between the inside and the outside of medium 2. However, alternatively, outer envelope 20 is omitted. For example, if medium 2 is a fluid or a gel, apparatus 1 can be at least partially immersed inside medium 2.

In this example, acoustically propagative medium 2 is a lossless and homogeneous medium.

Apparatus 1 comprises an ultrasound source 10, an ultrasound measurement unit 11 and an ultrasound scanner 12.

Ultrasound source 10 is adapted to generate focused ultrasound waves W upon receiving a command signal. For example, ultrasound source 10 comprises transducers, such as piezoelectric materials, adapted to convert an electrical command signal into a vibration in order to generate a variable acoustical pressure field in its surroundings.

In this example, apparatus 1 further comprises an ultrasound wave generator 101 connected to ultrasound source 10 and adapted to generate and amplify a command signal. For example, wave generator 101 comprises an electrical signal generator and an amplifier circuit forming together a driver circuit of ultrasound source 10. Ultrasound wave generator 101 is advantageously commanded by a programmable electronic calculator, not illustrated. For example, ultrasound wave generator 101 is the generator sold under the commercial reference "Ablatherm® by Edap-TMS".

Ultrasound source 10 is preferentially adapted to generate ultrasound waves with a wave frequency comprised between 100 kHz and 150 MHz.

In this example, ultrasound source 10 is also adapted to generate high-intensity focused ultrasound waves. Optionally, ultrasound source 10 may also be adapted to generate unfocused ultrasound waves and/or low intensity ultrasound waves.

For example, ultrasound source 10 is a therapeutic ultrasound transducer.

Ultrasound source 10 is placed in a so-called emission region 21, here at the outer envelope 20 of acoustically propagative medium 2, for example in direct contact with envelope 20, and is arranged so that the emitted ultrasound waves W1 propagate inside acoustically propagative medium 2. On FIG. 1, axis X10 denotes an emission axis of ultrasound source 10. For example, axis 10 is a symmetry axis of the acoustic beam 4 of waves generated by wave generator 101. Axis Y10 is perpendicular to axis X10. In this example, axis X10 is arranged horizontally and axis Y10 is arranged vertically.

On FIG. 1, the acoustic beam formed by ultrasound waves W1, as they propagate inside acoustically propagative medium 2, is illustrated as dashed lines and bears the numerical reference 4. In this example, acoustic beam 4 is focused on a target region 23 of acoustically propagative medium 2 so as to deliver as much energy as possible to acoustically propagative medium 2 in target region 23 in order to create a lesion there.

Ultrasound measurement unit 11 includes a sensor array 111, comprising an array of individual sensors 112 arranged along an orientation axis Y11. For example, said orientation axis Y11 is arranged vertically. Here, axis Y11 is parallel to axis Y10. Axis X11 denotes an alignment axis arranged perpendicularly to axis Y11. For example, axis X11 is parallel to axis X10.

Each individual sensor 112 is adapted to measure the acoustic field values in its immediate surroundings and, more specifically, along a measurement surface. For example, individual sensors 112 are identical to each other and differ only by their position in sensor array 111. In this example, each individual sensor 112 comprises a piezoelectric transducer, for example made of a layer of piezoelectric material defining a measurement surface and being connected to a voltage measurement apparatus. When the acoustic pressure field near the measurement surface changes over time, it induces a deformation of the piezoelectric layer. In turn, the piezoelectric layer generates a voltage whose variation in time is representative of the pressure variation at said measurement surface. This voltage is then recorded over a short time interval, for example using an analogue-to-digital converter, and converted into a measurement signal waveform.

Individual sensors 112 may alternatively be based on transducers of a different technology, such as capacitive micromachined ultrasonic transducers.

In this example, individual sensors 112 are aligned along orientation axis Y11, with their respective measurement surfaces orientated in the direction of alignment axis X11. For example, the height h 1 of sensor array 111, measured along orientation axis Y11, is equal to 4 cm.

Ultrasound measurement unit 11 is placed at a reception region 22 of medium 2, where it can receive the ultrasound waves emitted by ultrasound source 10.

In this example, reception region 22 is located opposite to the emission region 21. In this case, preferably, reception region 22 is aligned with emission region 21, along axis X10 so that axis X10 and axis X11 coincide with each other.

However, when the path of acoustic beam 4 is not a straight line inside medium 2, the emission region 21 and the reception region 22 are not necessarily aligned. In that case, axis X10 does not coincide with axis X11. For example, reception region 22 and emission region 21 are located side by side.

Optionally, an acoustical mirror, such as a reflecting material adapted to reflect or deflect acoustic beam 4 within medium 2, e.g. a sheet of metal, may be placed at a specific location inside medium 2, for example behind an organ of interest, so as to purposefully deflect acoustic beam 4.

Individual sensors 112 are arranged so as to generate voltage signal waveform values representative of acoustic field values at reception region 22. Here, individual sensors 112 are facing ultrasound source 10, for example with their measurement surface positioned at reception region 22 and turned towards outer envelope 20 and facing ultrasound source 10. For example, individual sensors 112 are in contact with outer envelope 20.

Reception region 22 is preferably located at a position corresponding to the propagation of acoustic beam 4, so that a significant proportion of the acoustic power emitted by source 10 can be collected by the respective measurement surfaces of the individual pressure sensors 112 of sensor array 111. For example, the power thus collected is said to be significant if it at least equal to 50% of the emitted power, preferably at least 75% of the emitted power, preferably still at least 90% of the emitted power. The higher the proportion of acoustic power, the better the accuracy of the imaging of ultrasound waves W1 by apparatus 1.

In this example, both the ultrasound source 10 and the ultrasound measurement unit 11 are located outside medium 2. However, source 10 and/or measurement unit 11 may be at least partially inserted within medium 2 if the latter is a gel or a fluid.

Preferably, ultrasound measurement unit 11 is adapted to acquire simultaneously, by at least 95% of the sensors 112 of sensor array 111, preferably by all sensors 112, the voltage signal waveform values at reception region 22.

However, in other embodiments, ultrasound measurement unit 11 is adapted to acquire simultaneously, by at least some of the sensors 112, for example by a predefined subgroup of sensors 112, the voltage signal waveform values at a portion of reception region 22.

Figure 2:
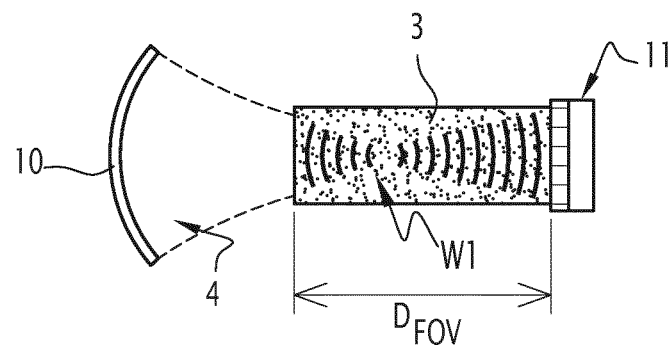
FIG. 2 is a simplified diagrammatic representation of a field of view of the apparatus of FIG. 1.

Here, as illustrated in FIG. 2, ultrasound measurement unit 11 has a two-dimensional field of view 3 along the propagation direction of acoustic beam 4. In this example, field of view 3 extends along a geometrical plane, noted P, parallel to axis X11 and to orientation axis Y11. The length of field of view 3, measured along alignment axis X11, here along the path followed by acoustic beam 4, bears the reference "$D_{FOV}$". The value of length $D_{FOV}$ depends on the duration of the measurements performed by ultrasound measurement unit 11, as explained in what follows.

Optionally, each individual sensor 112 of sensor array 111 is able to emit one or several additional mechanical waves, for example ultrasound waves, upon receiving a command signal. Said waves are distinct from waves W1 generated by source 10. In that case, measurement unit 11 is able to operate in an "active mode", for example in a pulse-echo mode, by emitting such additional ultrasound waves inside medium 2 and then, in response, measuring, using the same sensor array 111, reflected ultrasound waves propagating in medium 2 towards the reception region 22. This way, a background image of medium 2 itself can be acquired. In this active mode, sensor array 111 can both emit waves and measure voltage signal waveform values, albeit not necessarily simultaneously.

Measurement unit 11 is also able to operate in a "passive mode", distinct from the active mode, in which it does not emit any ultrasound wave and merely measures the voltage signal waveform values using individual sensors 112 of sensor array 111. In this embodiment, measurement unit 11 is meant to operate only in the passive mode.

Ultrasound scanner 12 is adapted to acquire and process data measured by ultrasound measurement unit 11, in order to generate automatically at least one image, noted I, of the spatial distribution, along geometrical plane P, of the acoustic field values in medium 2.

In this example, ultrasound scanner 12 comprises a signal reception unit 121, a signal processing unit 122, an image generation device 123 and a display device 124. In this illustrative example, ultrasound scanner 12 is the ultrasound scanner sold under the commercial reference "EPIQ 7®" by PHILIPS HEALTHCARE.

For example, ultrasound scanner 12 comprises an electronic calculator, not illustrated, including an arithmetic logic unit, a graphical processing unit and a data recording medium able to store executable instructions. Signal processing unit 122 and image generation device 123 are implemented as software modules and executed by said electronic calculator.

Alternatively, signal processing unit 122 and/or image generation device 123 are hardware devices each comprising a programmable electronic calculator.

Signal reception unit 121 is connected to sensor array 111 so as to collect the measurement signals generated by each individual sensor 112. Said measurement signals may be collected only during so-called signal acquisition intervals, as explained in what follows.

Signal processing unit 122 is adapted to process and condition the measurement signals acquired by signal reception unit 121, and to calculate the acoustic wave field in at least one spatial position "M", and preferably at a plurality of positions so as to form an image of said acoustic wave field.

In a first example, signal processing unit 122 is programmed to calculate the acoustic field using a time reversal algorithm. Using this technique, acoustic beam 4 is reconstructed from the measurement signals using a discrete approximation of Rayleigh's integral, as follows:

$$v_k(t) = s_k(t) * h_k(t) \quad (1)$$

and $$\Phi_{TR}(M, t) = \frac{1}{2\pi} \sum_k \frac{v_k(t + r_k(M)/c)}{r_k(M)} S_k \quad (2)$$

where:
the star symbol (*) denotes a convolution operation,
$\phi_{TR}(M,t)$ is the estimated value of velocity potential at a position "M" inside soft material 2, "M" being the position vector of the observation point, here a pixel position within the field of view, and at a time "t" that can be chosen arbitrarily. A plurality of images can be created by varying time "t", said plurality of images can be assembled in a movie animation showing the propagation of the mechanical wave in the medium,
"$v_k(t+r_k(M)/c)$" is the normal particle velocity on the $k^{th}$ element of the sensor array at time "$t+r_k(M)/c$"
"$s_k(t)$" is the voltage signal waveform measured on the $k^{th}$ element of the sensor array at time "t",
"$h_k(t)$" is the impulse response of the $k^{th}$ element of the sensor array at time "t". It can be measured experimentally, for example using the stepped plane wave method described in Lakestani F et al. "Generation of a stepped ultrasonic plane wave: Application to piezoelectric transducer calibration". J Phys D: Appl Phys 1976; 9: 547-54, "$r_k(M)$" is the distance between the center of the $k^{th}$ element of the sensor array 111 and location "M", "c" is the propagation speed of sound inside soft material 2, "$S_k$" is the surface of the $k^{th}$ elements of the sensor array 111

In the specific case of a monochromatic wave field with a single frequency f, the convolution product "$v_k(t) = s_k(t) * h_k(t)$" can be replaced by equation "$v_k(t) = K_k \, s_k(t + \varphi_k/2\pi f)$", where $K_k$ is a real and positive constant ratio, and $\varphi_k$ is a phase shift. This equation is less computationally-intensive than the convolution product and therefore requires less computational resources. It can also be used in the case of a wave field whose frequency contents spans over a narrow frequency bandwidth, with the assumption that sensor sensitivity is constant over that specific bandwidth.

Finally, other important acoustics parameters, such as pressure p(M,t), all three components of particle velocity vector $\vec{v}(M,t)$, and all three components of the intensity vector $\vec{I}(M,t)$ can be calculated from the velocity potential $\phi$, using equations:

$$p = -\rho \partial \Phi / \partial t \quad (3)$$

$$\vec{v} = \overrightarrow{grad}(\Phi) = \vec{\nabla}\Phi \quad (4)$$

$$\vec{I} = p\vec{v} \quad (5)$$

where $\rho$ is the density of soft material 2.

In a second example, signal processing unit 122 is programmed to generate the image using a dynamic receive focusing (or "beam forming") image reconstruction algorithm. An example of such an algorithm is described by P.N.T. Wells in "Biomedical Ultrasonics", chapter 6.10.c, Academic Press, London, 1977, ISBN 0-12-742940-9. Using this technique, the values of the measured signals received from the individual respective sensors 112 of sensor array 11 are shifted in time and summed, using the following formulas:

$$b(M) = \sum_k s_k\left(\frac{d(M) + r_k(M)}{c}\right) \quad (6)$$

The beamforming algorithm described by equation (6) is implemented in all medical ultrasound scanners. However, the resulting value b(M) is not representative of the acoustic field, and a correction factor is needed. Assuming all sensor elements have same surface $S_k = S$ and same sensitivity $K_k = K$, the correction factor is:

$$\Phi_{BF}(M, t_M) = \frac{fKS}{d(M)} b(M) \quad (7)$$

where:

b(M) is the value of the post-beamforming ultrasound signal at a position "M" inside soft material 2, "M" being the position vector of the observation point, here a pixel position within the field of view. In medical ultrasound imaging, image b(M) is commonly called the beamformed radio-frequency image, or the beamformed RF image.

Figure 9:
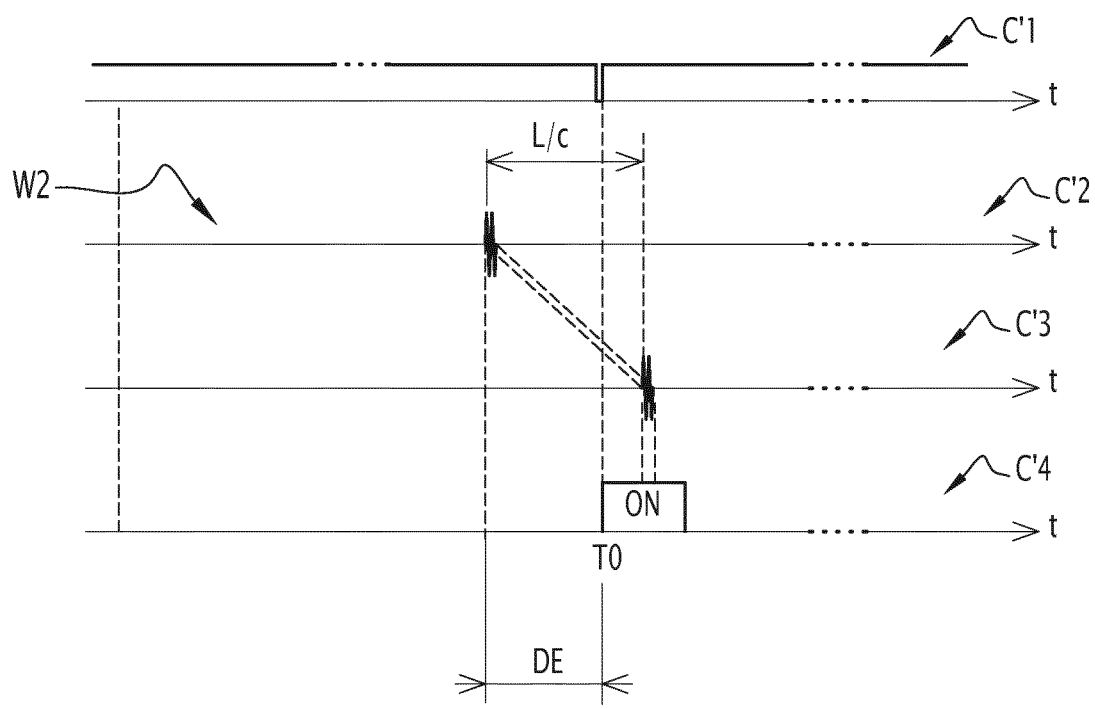
FIG. 9 is a simplified illustration of the synchronization between emission and measurement of transient mechanical waves, using the apparatus of FIG. 5.

$\phi_{BF}(M, t_M)$ is the value of an acoustic velocity potential at time "$t_M$" and at a location "M" inside soft material 2, where time $t_M$ is defined as $t_M = d(M)/c$, "$s_k((d(M) + r_k(M))/c)$" is the value of the voltage signal measured at time $t = (d(M) + r_k(M))/c$ on the $k^{th}$ element of the sensor array, "$r_k(M)$" is the distance between the center of the $k^{th}$ element of the sensor array 111 and location "M", "d(M)" is the smallest distance between the center of the elements of the sensor array 111 and location "M", and is defined as $d(M) = \min(r_k)$, "c" is the propagation speed of sound inside soft material 2, "f" is the frequency of the ultrasound field to be measured, "K" is the sensitivity of the elements of the sensor array at frequency f "S" is the surface of the elements of the sensor array The acoustic field value $\Phi_{BF}(M,t)$ can be calculated at any position M and, optionally, at any arbitrary time "t" by use of a synchronization unit, as will be described in what follows in reference to the embodiment of FIG. 9, and setting delay DE equal to $t_M - t$. Finally, the entire wave field $\Phi_{BF}(M,t)$ can be reconstructed by varying the trigger delay DE and repeating the acquisition, so as to cover all possible values for M and t.

The dynamic receive focusing algorithm described by equations (6) and (7) is not as accurate as the time-reversal algorithm. However it is advantageous because equation (6)—which is computationally intensive—is already implemented in conventional medical ultrasound scanners, typically with fast and efficient hardware or software. Therefore the invention can be implemented using a conventional ultrasound scanner, by retrieving the beamformed radio-frequency image, or its envelope, from that scanner and then calculating the velocity potential using equation (7).

In the case of conventional medical ultrasound scanners, where only the envelope e(M) of the beamformed RF image is available, then the envelope of a continuous acoustic field can be reconstructed using equation (8):

$$\|\Phi_{BF}(M)\| = \frac{fKS}{d(M)} e(M) \quad (8)$$

where $e(M) = \|b(M)\|$ is the envelope of the beamformed radio-frequency image. In medical ultrasound, e(M) is commonly called the amplitude of the grayscale ultrasound image, or amplitude of the B-mode image, or amplitude of the sonogram.

Other techniques are possible for generating the image, such as using a holographic reconstruction algorithm, as described in the previously described article by Maynard et al. Other reconstruction algorithms can also be used.

Preferably, signal processing unit 122 is adapted to account for the physical properties of medium 2, such as attenuation, speed of sound or nonlinearity, when generating the image.

Optionally, a signal or a data structure representative of said physical properties is acquired by transmitting a wave from the acoustic source 10 or from the acoustic measurement unit 11 operating in active mode, then receiving the acoustic signals with the acoustic measurement unit 11 and processing the signals to determine said physical properties, prior to implementing the method.

Image generation device 123 is programmed to generate at least one image I of the spatial distribution of the acoustic field calculated by signal processing device 122.

To this end, image generation device 123 is programmed to implement image reconstruction algorithms.

For example, generated image I is a digital image, made of a plurality of individual pixels, here forming a two-dimensional matrix. Each pixel has a spatial position and an intensity value. The intensity value of each pixel is representative, according to some predefined scale, of the acoustic field value at a location of soft material 2 associated to the pixel's spatial position.

Display device 124 is adapted to display the image generated by the image generation device 123. For example, display device 124 is a video screen integrated with ultrasound scanner 12. Alternatively, display device 124 may be distinct from ultrasound scanner 12, for example arranged in a remote location and connected to ultrasound scanner 12 by means of a data link.

Figure 3:
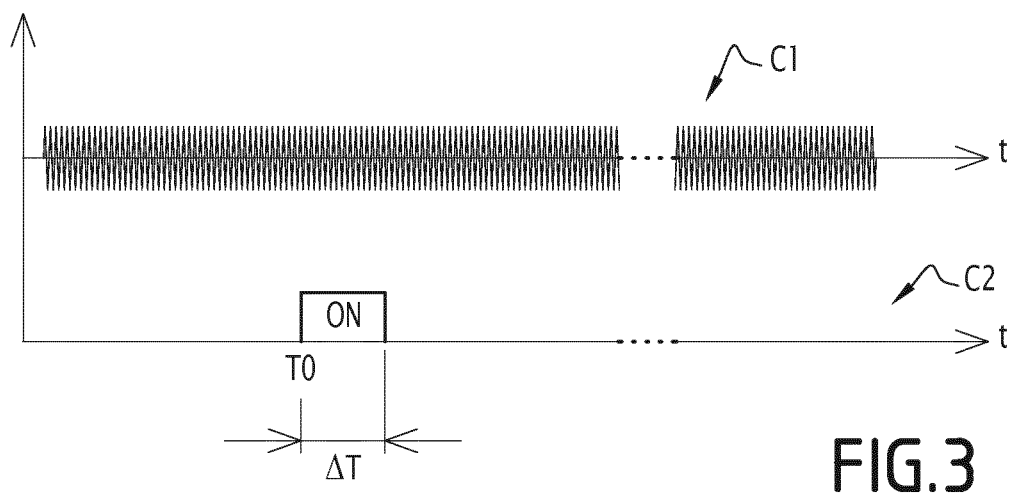
FIG. 3 is a simplified illustration of the measurement of continuous mechanical waves, for successive instants of time, using the apparatus of FIG. 1.

As illustrated on FIG. 3, in this example, ultrasound scanner 12 is programmed to measure data coming from ultrasound measurement unit 11 only during so-called signal detection intervals. The signal detection interval has a duration $\Delta T$. The signal detection interval begins at time T0.

On FIG. 3, curve C1 illustrates, as a function of time t, ultrasound waves W1 continuously emitted by ultrasound source 10. Curve C2 illustrates said signal detection interval, as a function of time t.

Optionally, ultrasound scanner 12 is programmed to repeatedly measure data using multiple detection intervals, beginning at instants T0, T1, T2, . . . , Tn, possibly with a predefined repetition frequency preferably comprised between 1 Hz and 10 kHz. This frequency corresponds to the frequency at which the reconstructed acoustic field is updated.

Figure 4:
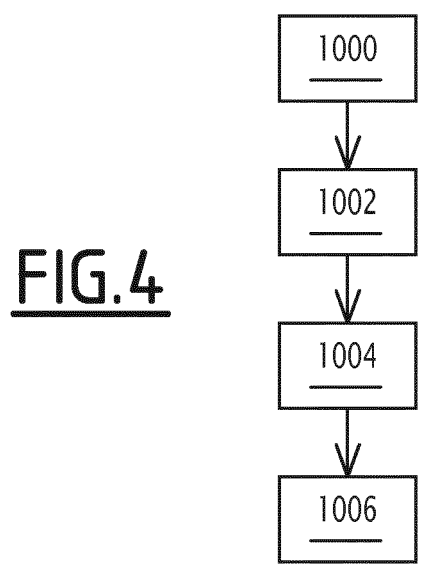
FIG. 4 is a flow-chart illustrating a method according to the invention for imaging in real time the propagation of an mechanical wave in an acoustically propagative medium, using the apparatus of FIG. 1.

An example of a method for imaging in real time the propagation of ultrasound wave W1 in medium 2 using apparatus 1 is now described, in reference to the flow chart of FIG. 4.

Initially, apparatus 1 and medium 2 are provided, with ultrasound source 10 positioned at emission region 21 and ultrasound measurement unit 11 positioned at reception region 22.

During a step 1000, ultrasound waves W1 are emitted in medium 2 by ultrasound source 10, for example by having wave generator apply a command signal to ultrasound source 10. As an example, ultrasound waves W1 are emitted continuously, for a duration longer than 30 s or 1 min.

Then, during a step 1002, measurement unit 11 measures the voltage signal waveform at reception region 22. This measurement comprises the simultaneous acquisition, by individual sensors 112 of sensor array 111, of voltage signal waveform values at reception region 22. This simultaneous acquisition is repeated for successive instants in time, for example during the measurement duration.

In this embodiment, this simultaneous acquisition is performed simultaneously for at least 95% of the individual sensors 112 of sensor array 111, preferably still for all the individual sensors 112 of sensor array 111.

During this step 1002, in this embodiment, measurement unit 11 operates in the passive mode.

At the end of step 1002, voltage signal waveform values acquired during the measurement duration are representative of the acoustic field values in medium 2.

During a step 1004, acoustic field values in medium 2 are automatically calculated, by signal processing unit 122 and, based on the voltage signal waveform measured.

Then, during a step 1006, an image I of the acoustic field medium 2 is automatically generated, for example using image generation device 123, based on the acoustic field values calculated during step 1004, is automatically displayed on display device 124. The image is then optionally displayed on display device 124.

In this exemplary embodiment, image I is a two-dimensional image. In alternative embodiments, generated image I is a three-dimensional object. Image I may also be raw image data that is able to be automatically processed by additional devices, for example in order to generate an enhanced image. To this end, the image generation device 123 may be arranged remotely from the rest of apparatus 1.

In this example, during step 1006, the generation of image I comprises the generation of image data, for example a digital image or an analog video signal, based on the calculated acoustic field values. This generated image I is then displayed by providing said image data to a hardware controller of display device 124. Steps 1002 and 1004 may be repeated continuously, so as to allow visualization in real time of ultrasound waves W1 in medium 2. For example, steps 1002, 1004 and 1006 are repeated for each instant T0, T1, T2, . . . , Tn.

Due to the position of sensor array 11 relative to emission region 21, and the fact that the acquisition is performed simultaneously for individual sensors 112, the propagation of ultrasound waves W1 between emission region 21 and reception region 22 is imaged in real time. Image generation device 124 allows for a real-time and accurate generation of image I. This method can be used reliably in soft materials, including optically opaque ones, as well as with ultrasound waves of high intensity.

This method, as well as apparatus 1, can advantageously be used in clinical settings, to monitor in real time the effect of a beam of ultrasonic waves applied to soft material 2, allowing for a quick correction of the focusing properties of the beam if needed. This method can nonetheless be used with any acoustically propagative medium and in non-clinical settings, for example for performing non-destructive testing in industrial settings.

Figure 5:
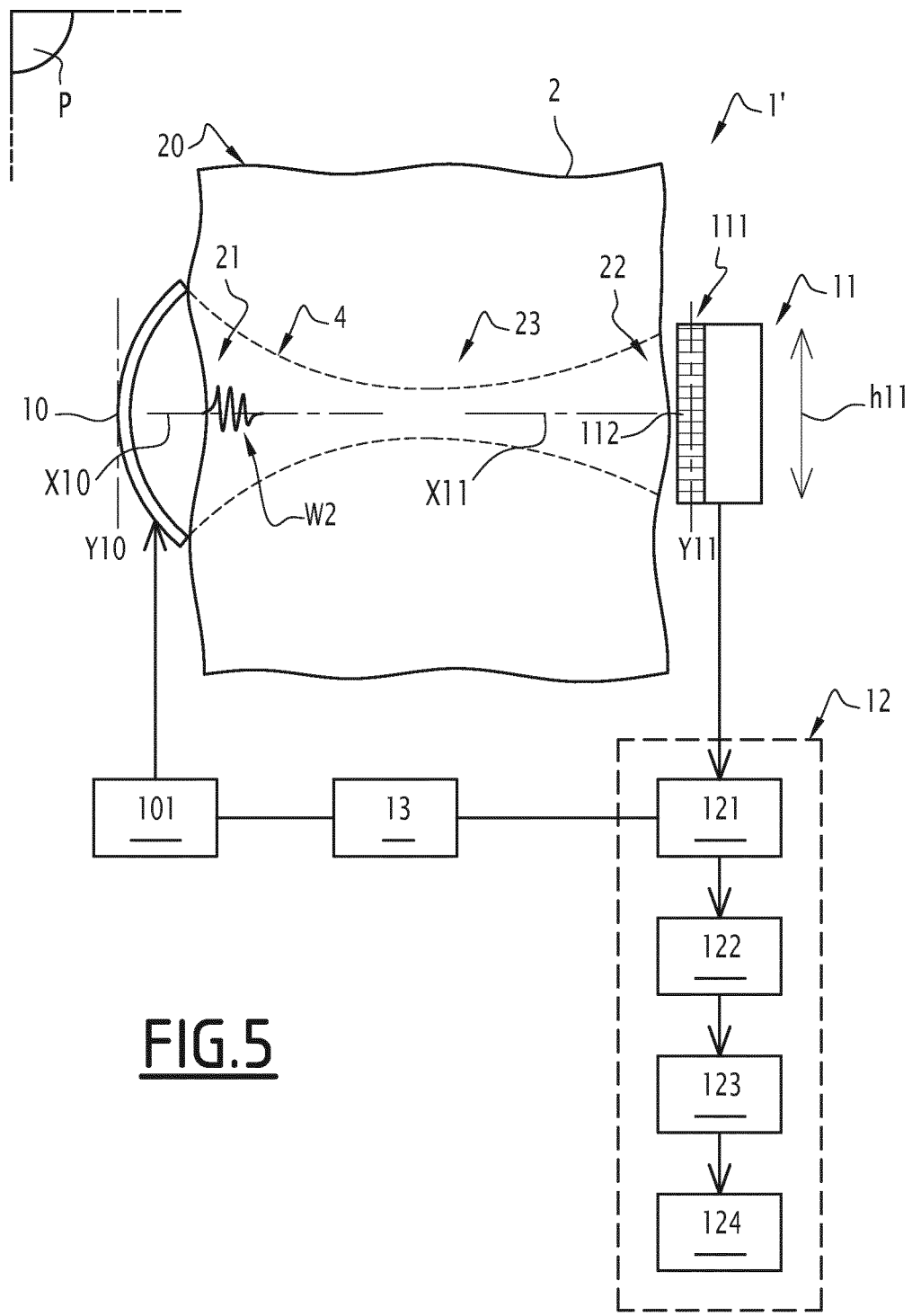
FIG. 5 is a simplified diagrammatic representation of another embodiment of the apparatus of FIG. 1 according to the invention, in which the emission and reception of mechanical waves are synchronized.

FIG. 5 shows an apparatus 1' according to another embodiment of the invention. The elements of apparatus 1' which are similar to that of apparatus 1 bear the same references and are not described in further detail in what follows, given that the description above can be transposed to these elements.

Apparatus 1' is similar to apparatus 1, except that it further comprises a timing control unit 13 adapted to synchronize in time the acquisition of voltage signal waveform values by sensors 112 with the emission of ultrasound waves W2 by ultrasound source 10.

In the meaning of this invention, "synchronization" means that a controllable time delay is introduced between the emission of an ultrasound wave or of a train of ultrasound waves by ultrasound source 10 and the signal detection interval during which said ultrasound wave or train of ultrasound waves is expected to arrive at reception region 22.

More specifically, timing control unit 13 is programmed to perform this synchronization by controlling the delay between the beginning of each signal detection interval of ultrasound measurement unit 11 and the beginning of the emission of ultrasound waves W by ultrasound source 10, for example by means of a trigger signal.

For example, timing control unit 13 is connected to signal reception unit 121 and to wave generator 101 and is adapted to send a trigger signal to ultrasound scanner 12. Timing control unit 13 is also adapted to detect when wave generator 101 commands the emission of ultrasound waves W2.

Apparatus 1' is well suited for imaging ultrasound waves having a short duration, such as so-called transient waves, emitted during a short duration. Typically, said waves W2 are too short to be adequately imaged using apparatus 1 without synchronization.

For example, as illustrated in FIGS. 6 to 9, apparatus 1' is used to image transient ultrasound waves W2. The distance between ultrasound source 10 and ultrasound measurement unit 11 bears the reference "L" and is measured as the shortest path followed by acoustic beam 4 between source 10 and reception unit 11. Time interval L/c is the time of flight of wave W2 from the source 10 to the reception unit 11.

Figure 6:
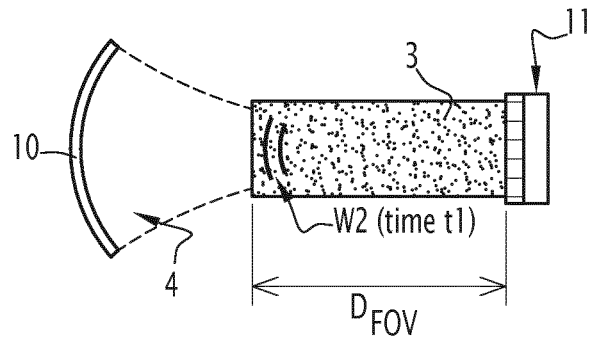
FIGS. 6, 7 and 8 are simplified diagrammatic representation of a field of view of the apparatus of FIG. 5 for different values of a reconstruction time "t"
Figure 7:
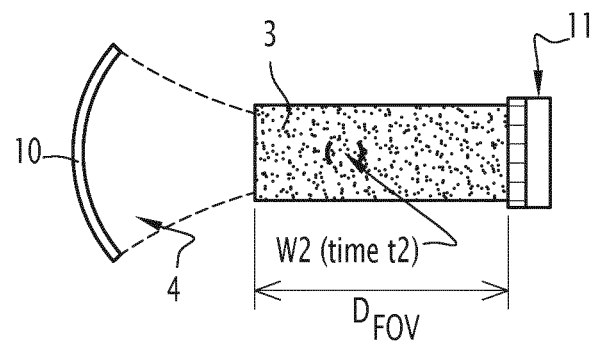
Figure 8:
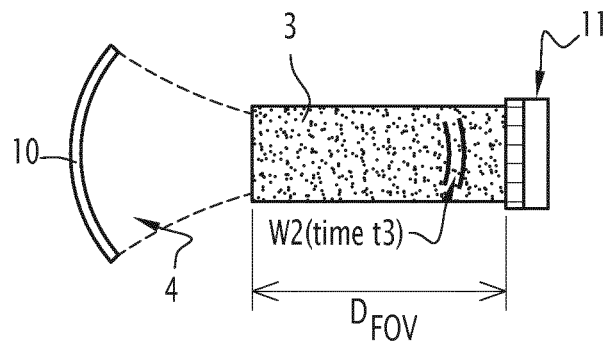

In the example of FIGS. 6 to 8, the acoustic field values are reconstructed based on voltage signal waveform values measured during the detection interval, and varying time "t" in equation (2). Here time "t" takes different values, respectively noted "$t_1$", "$t_2$" or "$t_n$". In this example, only three such values "$t_1$", "$t_2$" or "$t_n$" are described, however the number of values may be chosen differently, for example to cover successively the entire field of view 3.

FIG. 9 illustrates an example of synchronization between ultrasound source 10 and ultrasound measurement unit 11 for imaging said transient ultrasound wave W2.

Curve C'1 illustrates a trigger signal generated by timing control unit 13 for commanding ultrasound scanner 12. This trigger signal alternates periodically between an active value and an inactive value. Each time the trigger signal switches from an inactive value to an active value, ultrasound scanner 12 initiates a signal detection interval having a predefined duration, said signal detection intervals being similar to those described previously. Thus, each transition from an inactive value to an active value corresponds to one of instants T0, T1, T2, . . . , Tn.

Curves C'2 and C'3 illustrate, as a function of time t, several successive ultrasound waves W2 emitted periodically, shown respectively at emission region 21 and at reception region 22. The curve C'3 corresponds to curve C'2 shifted in time by an offset value equal to L/c, which is the time needed for each wave W2 to travel from ultrasound source 10 to measurement unit 11 inside soft material 2.

Curve C'4 illustrates one signal detection interval of ultrasound measurement unit 11 as a function of time t. The detection interval, here beginning at time T0, is illustrated here with the label "ON".

In this example, timing control unit 13 is programmed to detect the emission of an ultrasound wave W2 by ultrasound source 10, and then, in response, to command the beginning of a signal detection interval after a delay equal to DE. Preferably, delay DE is lower than or equal to L/c. In other words, the signal detection interval occurs after emission of an ultrasound wave W2, with a delay equal to DE after emission of said ultrasound wave W2. Optionally, the emission of ultrasound waves W2 is done periodically by ultrasound source 10, with a frequency equal to that of the frequency repetition of signal detection intervals.

Due to this synchronization, each ultrasound wave W2 arrives at reception region 22 during a signal detection interval, i.e. when ultrasound measurement unit 11 is activated and when ultrasound scanner 12 is able to acquire data measured by ultrasound measurement unit 11.

The method for imaging in real time the propagation of ultrasound waves in soft material 2 using apparatus 1' is similar to that of FIG. 4, except that during step 1002, the acquisition of voltage signal waveform values by individual sensors 112 is synchronized in time with the emission of the ultrasound waves by the ultrasound source 10, using timing control unit 13.

Figure 10:
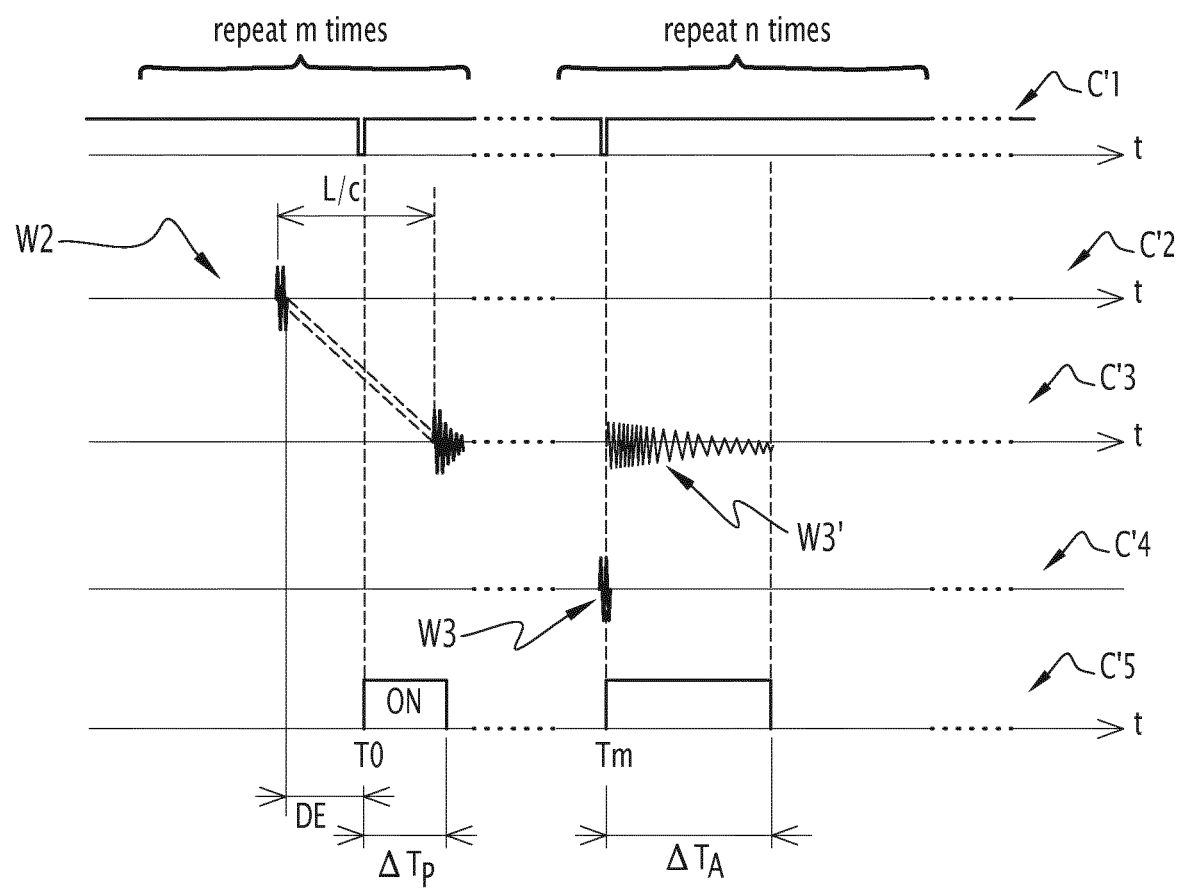
FIG. 10 is a simplified illustration of an interlaced operation mode in which the mechanical waves are imaged alternatively with the medium itself, using an acoustic measurement unit of the apparatus of FIG. 5.

FIG. 10 illustrates another embodiment of the invention, in which the synchronization of apparatus 1' is taken advantage of. In this FIG. 10, curves C"1, C"2, C"3 and C"5 are similar, respectively, to curves C'1, C'2, C'3 and C'4 of FIG. 9. Curve C"4 corresponds to the amplitude, as a function of time, of ultrasound waves W3 emitted by measurement unit 11.

In this embodiment, named as "interlaced mode", measurement unit 11 is commanded, for example by ultrasound scanner 12 and by timing control unit 13, so as to operate alternatively between the passive mode and the active mode, in order to acquire an image of medium 2 itself, along with imaging the propagation of acoustic waves W2 in the same medium 2.

For example, this operation mode is similar to that of FIG. 9, called the passive mode, except that, in addition, at some time intervals, measurement unit 11 enters in the active mode in which it emits ultrasound waves W2 as described previously. For example, operation in passive mode is repeated "n" times, then operation in active mode is repeated "m" times, where m and n are integer numbers greater than or equal to 1. In passive mode, the detection intervals have duration ΔTP. In active mode, the detection intervals have duration ΔTA. Preferably, $\Delta TA = 2\Delta TP = 2D_{FOV}/c$, where $D_{FOV}$ is the depth of the field of view, as described previously. For example, each emission cycle of ultrasound waves W2 by source 10 is followed by an emission cycle of ultrasound waves W3 by measurement unit 11, corresponding to case n=m=1.

Measurement unit 11 then measures the corresponding reflected waves W3' during subsequent measurement intervals. In this example, measurement intervals of duration ΔTP corresponding to the detection of ultrasound wave W2 at reception region by measurement unit 11 alternate with measurement intervals of duration ΔTA corresponding to the detection of reflected ultrasound waves W3' by measurement unit 11.

Therefore, in this embodiment, additional steps are executed after steps 1000 and 1002, during which waves W3 are emitted and the corresponding reflected waves W3' are measured by measurement unit 11. During step 1004, a corresponding background image of the medium 2 itself is generated, based on the voltage signal waveform values associated to reflected waves W3'.

This background image is then combined with the image of the spatial distribution of the acoustic field values associated to waves W2, in order to generate a composite image. This way, structural features of medium 2, such as inclusions or defects, or organs of interest in the case of biological tissues, can be visualized in the combined image along with the propagation of ultrasound waves W2.

Signal processing unit 122 and image generation device 123 are programmed in consequence.

Figure 11:
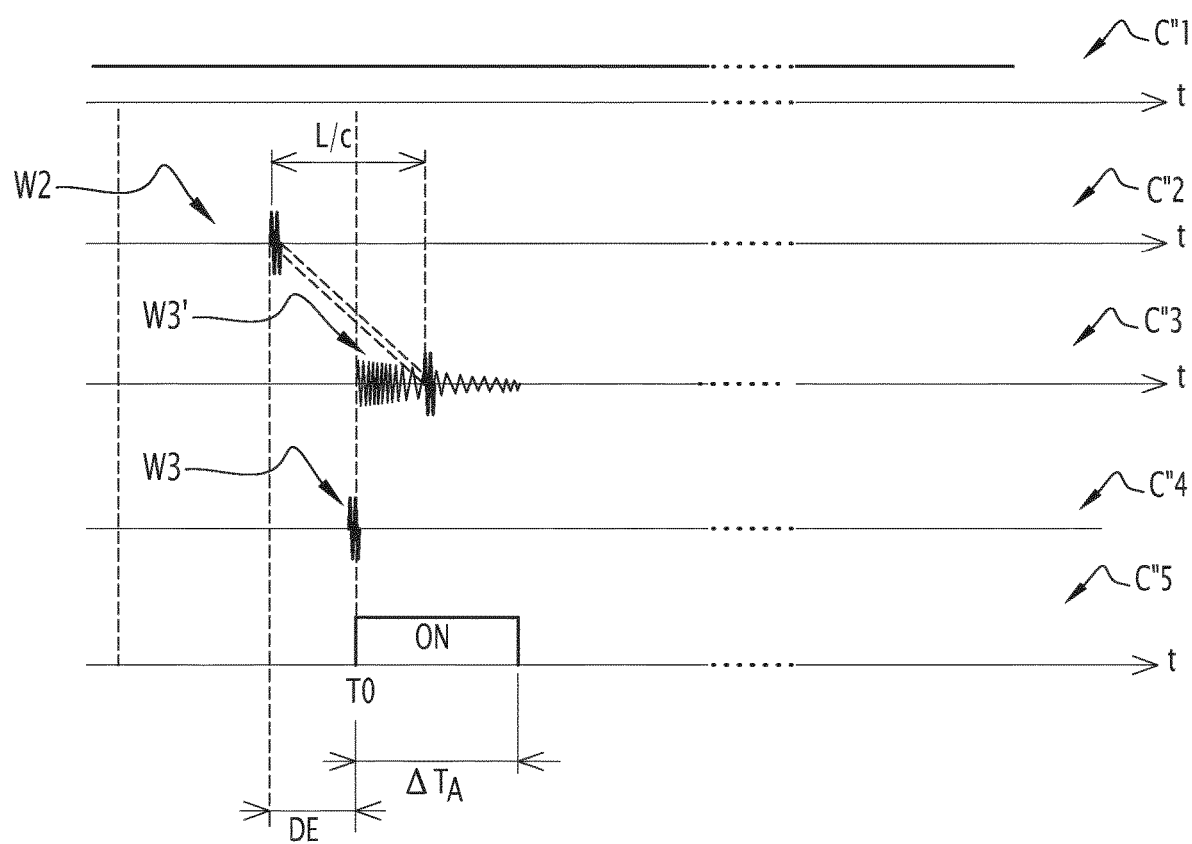
FIG. 11 is a simplified illustration of a dual-mode operation mode in which the mechanical waves are imaged simultaneously with the medium itself using an acoustic measurement unit of the apparatus of FIG. 5.

FIG. 11 illustrates another embodiment in which the synchronization of apparatus 1' is taken advantage of. This embodiment is named as "dual mode" and is similar to that of FIG. 10, except that ultrasound source 11 is now commanded so as to operate permanently in the active mode, in order to acquire an image of medium 2 itself by emitting ultrasound waves W3 and measuring corresponding reflected waves W3', simultaneously with imaging the propagation of acoustic waves W2 in the same medium 2. This way, structural features of medium 2 can be displayed in the generated image.

In this example, measurement intervals have a same duration ΔTA equal to $2D_{FOV}/c$, and delay DE is preferably chosen so that DE is lower than or equal to L/c.

In this embodiment, instead of having two separate steps, measurement step 1002 comprises the acquisition of the voltage signal waveform values at reception region corresponding to the combined effect of ultrasound waves W2 and reflected waves W3'. Optionally, the method further comprises a processing step for automatically separating the contribution of ultrasound waves W2 from the contribution of ultrasound waves W3'. This operation is for example performed by signal processing unit 122.

Signal processing unit 122 and image generation device 123 are programmed in consequence.

According to a first exemplary possibility, ultrasound waves W2 and W3' are separated in the frequency domain, for example using a Fourier transform or a wavelet transform. This first possibility is preferably used where the frequency of waves W2 is different from the frequency of waves W3 and/or where waves W2 have a narrow bandwidth. The second possibility is preferably used where the shape of waves W2 is different from the shape of waves W3. According to another exemplary possibility, at least one of ultrasound waves W2 and W3 is transmitted using coded excitation, for example using complementary Golay codes as described by M. Golay in "Complementary series", IRE Transactions on Information Theory, 1961; 7(2): 82-87.

Preferably, the background image of medium 2 is then obtained using conventional beamforming reconstruction methods, while a series of images showing the propagation of ultrasound wave W2 is reconstructed with the time-reversal reconstruction method.

This dual mode can also be used as well when imaging continuous waves using apparatus 1', as described previously.

Figure 12:
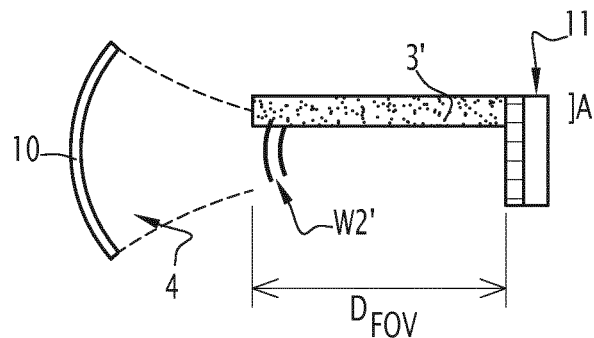
FIGS. 12, 13 and 14 are simplified diagrammatic representations of a field of view of the apparatus of FIG. 5 for different values of time in a line-by-line acquisition mode.
Figure 13:
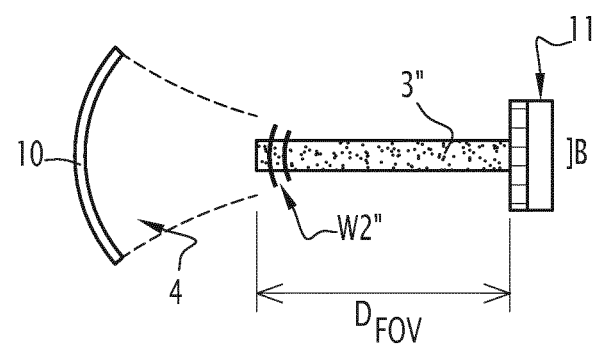
Figure 14:
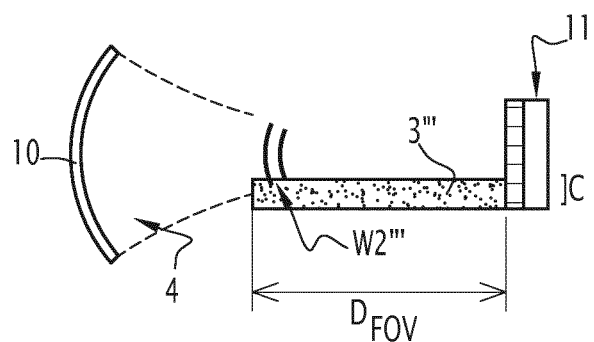

FIGS. 12 to 14 illustrate yet another embodiment of the invention, in which the synchronization of apparatus 1' is taken advantage of. This embodiment is similar to that of FIGS. 6 to 9, here for a fixed value of distance d, except that, during step 1002, the measurement is performed only by a predefined sub-group of the individual sensors 112. Thus, only a portion of field of view 3 is imaged. Therefore, steps 1000 and 1002 are repeated in succession in order to generate waves W1 and, each time, imaging a different portion of field of view 3 using a different predefined sub-group of the individual sensors 112, until the entire field of view 3 can be imaged. During each measurement step 1002, the simultaneous acquisition of voltage signal waveform values is thus performed only by the individual sensors 112 belonging to said predefined sub-group.

In this illustrative example, individual sensors 112 are shared between three distinct subgroups A, B and C. To simplify this example, the sensors 112 of each sub-group A, B and C are adjacent and the subgroups A, B and C are not overlapping. However, this is not necessarily the case and any arbitrary number of sub-groups may be defined.

This acquisition step is illustrated on FIGS. 12 to 14, respectively performed successively by each sub-group A, B, C of individual sensors 112 for imaging, respectively, portions 3', 3" and 3'" of field of view 3. The delay DE is kept constant for each step, thus imaging a portion of the emitted waves, here noted W2', W2" and W2'" respectively, in a same region of medium 2.

The images of the wave propagation can then be generated from the voltage signal waveform values successively acquired by the different sub-groups A, B, C of individual sensors 112. Image generation device 123 is further programmed to this end.

According to a first exemplary possibility, the images are generated at once during step 1004, after steps 1000 and 1002 have been repeated until all individual sensors 112 of sensor array 111 have been used.

According to a second exemplary possibility, the complete images of the field of view 3 are generated progressively, by repeating step 1004 every time steps 1000 then 1002 are repeated, to generate successive portions of the image. During each step 1004, a portion of the image I, i.e. an image of the corresponding portion 3', 3" or 3'" of field of view 3, is generated using the measured voltage signal waveform values acquired by the sub-group of sensors 112 during the previous step 1002. Steps 1000, 1002 then 1004 are repeated until the image I of the entire field of view 3 is generated, even if one or several individual sensors 112 are used more than once.

This embodiment has the advantage that the generation of the image using data acquired by the successive sub-groups requires less hardware resources than generating an image using data acquired simultaneously by all sensors of the sensor array 111. Therefore, it can be easily implemented on low-end ultrasound scanners 12. While these successive acquisition steps take more time than a simultaneous acquisition by all individual sensors 112, the method is still faster and less cumbersome than moving a hydrophone around space.

According to yet another embodiment, not illustrated, ultrasound measurement unit 11 comprises a two-dimensional sensor matrix comprising several adjacent sensor arrays, each comprising an array of individual sensors arranged along parallel orientation axes, for example parallel to orientation axis X11. Said two-dimensional sensor matrix replaces sensor array 111 and plays a similar role as sensor array 111 within ultrasound measurement unit 11. For example, individual sensors forming said two-dimensional sensor matrix are similar to individual sensors 112, and each array is similar to sensor array 11.

As a consequence, field of view of ultrasound measurement unit 11 is a three-dimensional field of view having a prismatic shape and, in the case where axes X10 and X11 are aligned, also comprising geometrical plane P.

Then, during step 1004, the generated image is a three-dimensional image of the spatial distribution of the acoustic field inside a volume of soft material 2, between emission region 21 and reception region 22.

This embodiment is applicable to either apparatus 1 or apparatus 1' and may be used in any of the previously described embodiments. Optionally, this two-dimensional sensor matrix may be used in a way similar to that of the embodiment of FIGS. 12 to 14, by defining sub-groups each corresponding to a one-dimensional array of sensors within the two-dimensional sensor matrix.

In an exemplary embodiment, the sensor array is mounted on a motorized table composed of translation stages, rotation stages, or a combination of such stages. The sensor array can be a linear array, or a matrix array, or any array. Three-dimensional imaging is performed by moving the sensor array to different positions. For each position, the sensor voltage waveforms are recorded, so that the total number of waveforms being acquired Nw is now equal to the number of sensor elements multiplied by the number of displacement positions. The acoustic field is calculated using equation (2), where index k now varies from 1 to Nw. Optionally, the image of the acoustic field is progressively updated after each displacement. This embodiment improves the accuracy of the reconstructed acoustic field, by means of artificially extending the surface of the receiver.

Alternatively, the acoustic source is mounted on a motorized stage, and the sensor array is mounted on a static holder or on another motorized system.

The above examples are described with respect to ultrasound waves. However, the invention may be applied to other mechanical waves, such as infrasound waves, for example for imaging applications in non-medical settings. In that case, apparatus 1 and/or 1' are adapted in consequence. For example, ultrasound source 10 is replaced by an acoustic source having a similar role. Ultrasound measurement unit 11 is replaced by an acoustic measurement unit having a similar role and comprising a sensor array including individual sensors suitable to operate in the corresponding frequency range. Ultrasound scanner 12 is replaced by an acoustic scanner having a corresponding role.

The embodiments and alternatives described above may be combined with each other in order to generate new embodiments of the invention.

The invention claimed is:

1. A method for imaging in real time the propagation of waves, including any of infrasound to ultrasound acoustic waves, in an acoustically propagative medium, comprising:
   a) emitting acoustic waves, from an acoustic wave source at an emission region of the acoustically propagative medium, toward a reception region of the acoustically propagative medium, the reception region being distinct from the emission region;
   b) measuring the acoustic waves as received at a plurality of locations in the reception region of the acoustically propagative medium, the measuring comprising:
      generating by a plurality of individual acoustic sensors positioned at the reception region, over a detection interval, respective voltage signal waveform values indicative of the acoustic waves as received, and
      performing by the individual acoustic sensors a succession of simultaneous acquisitions of the voltage signal waveform values, the simultaneous acquisitions being at instants of time in a succession of instants of time within the detection interval, and outputting a corresponding succession of simultaneously acquired voltage signal waveform values;
   c) calculating, by a programmable electronic calculator that is connected to an acoustic scanner connected to the plurality of acoustic sensors, a group of acoustic field values that represent an image of an acoustic beam of the emitted acoustic waves propagating in a region in the acoustically propagative medium between the emission region and the reception region, the calculating in accordance with a reconstruction algorithm and based on the succession of simultaneously acquired voltage signal waveform values and comprising the programmable electronic calculator executing calculation instructions, stored in a data recording medium connected to the programmable electronic calculator, which cause the programmable electronic calculator to perform the calculating in accordance with the reconstruction algorithm;
   d) generating, by the programmable electronic calculator or by another programmable electronic calculator connected to the acoustic scanner, a digital pixel image of the acoustic beam based at least in part on the group of acoustic field values, the generating comprising the programmable electronic calculator or the other programmable electronic calculator executing executable image generating instructions stored in the data recording medium, or in another data recording medium connected to the other programmable electronic calculator; and
   e) displaying the digital pixel image of the acoustic beam on a display connected to the acoustic scanner.

2. The method of claim 1, wherein step b) further comprises the acoustic scanner connected to the plurality of acoustic sensors performing the succession of simultaneous acquisitions over a detection interval that starts at a time instant and has a detection duration, and the method further comprises repeating a performing of a sequence comprising steps b) through d), over a next detection interval, having the detection duration and starting at another detection time instant, which is spaced in time from a most recent preceding detection time instant by a duration greater than the detection duration.

3. The method of claim 1, wherein:
   step a) further comprises generating, by a wave generator coupled to the acoustic wave source, an emission command, and the acoustic wave source, in response to the emission command, emitting the acoustic waves; and
   step b) further comprises synchronizing the succession of simultaneous acquisitions to the emitting the acoustic waves, the synchronizing comprising:
      detecting, by a programmable timing controller connected to the wave generator, a beginning of the emitting of the acoustic waves and, in response to the detecting, generating a trigger signal at a time delay relative to the detected beginning of the emitting the acoustic waves, the time delay being based on a propagation time of the acoustic waves from the emitting region to the reception region, and
      the plurality of acoustic sensors performing the succession of simultaneous acquisitions based, at least in part, on the trigger signal, over a detection interval that begins at a first field of view detection and has a detection duration,
   wherein the detecting the beginning of the emitting of the acoustic waves and the generating the trigger signal comprises an electronic processor of the programmable timing controller executing detection and trigger generation instructions stored in a data recording medium connected to the electronic processor of the programmable timing controller.

4. The method of claim 1, wherein the plurality of acoustic sensors are in a sensor array comprising switchable mode acoustic transducers, structured as switchable in response to a mode command between an active mode and a passive mode, and to perform:
   in the passive mode, as the acoustic sensors; and
   in the active mode, a pulse-echo sequence that includes emitting for an additional acoustic waves duration, the additional acoustic waves,
      generating reflection voltage signal waveform values indicative of reflections of the additional acoustic waves as received, and
      simultaneous acquisition of the reflection voltage signal waveform values,
   wherein the method further comprises steps:
   f) switching the plurality of switchable mode acoustic transducers to the active mode;
   g) performing, by the active mode acoustic transducers, an instance of the pulse-echo sequence, emitting the additional acoustic waves followed by generating, over a reflection measuring interval that starts at a reflection time delay after the emitting, reflection voltage signal waveform values indicative of reflections of the additional acoustic waves, as received;

h) performing, by the active mode acoustic transducers within the reflection measuring interval, a succession of simultaneous acquisitions of the plurality of the reflection voltage signal waveform values, each in the succession being at an instant of time in another succession of instants of time, the other succession of instants of time being in the reflection measuring interval, and outputting a corresponding succession of simultaneously acquired voltage signal reflected waveform values;

i) calculating by the programmable electronic calculator connected to the acoustic scanner, a group of reflected additional acoustic field values based on the succession of simultaneously acquired voltage signal reflected waveform values, comprising the programmable electronic calculator executing a reflection calculation configuration of the calculation instructions stored in the data recording medium connected to the programmable electronic calculator, wherein step d) further includes step d'), comprising generating of the digital pixel image further based, at least in part, on a combination of the group of acoustic field values and the group of reflected additional acoustic field values, and image generating instructions stored in the data recording medium connected to the programmable electronic calculator or in the data recording medium connected to the other programmable electronic calculator are configured to generate the digital pixel image as a superposition of the digital pixel image of the acoustic beam, based on the group of acoustic field values, and a digital pixel background image of the acoustically propagative medium, based on the group of reflected additional acoustic field values.

5. The method of claim 4, wherein the acoustic waves are coded acoustic waves, or the additional acoustic waves are coded additional acoustic waves, or the acoustic waves are coded acoustic waves that are coded according to a first coding and the additional acoustic waves are coded additional acoustic waves that are coded according to a second coding that is different from the first coding.

6. The method of claim 4, further comprising:
prior to switching the plurality of switchable mode acoustic transducers to the active mode, performing a passive mode sequence, comprising claim 1 steps a) through c), generating another group of acoustic field values;
performing, after the passive mode sequence, an instance of steps f) through i), generating another group of reflected additional acoustic field values;
performing an instance of step d'), generating another digital pixel image, based at least in part on a superposition of the another group of acoustic field values and the another group of reflected additional acoustic field values; and
performing an instance of step e), further based on the another digital pixel image.

7. The method of claim 1, wherein the emitted acoustic waves, having respective wave frequencies between 100 kHz and 150 MHz.

8. The method of claim 1, wherein the calculation instructions stored in the data recording medium connected to the programmable electronic calculator are configured to cause the programmable electronic calculator to calculate the group of acoustic field values as field of view acoustic field values, associated with a field of view having a depth that is based on the detection duration, and having a width and direction that is based on the respective locations of the individual acoustic sensors forming the plurality of individual acoustic sensors.

9. The method of claim 1, further comprising, prior to a first instance of steps a) through e):
arranging the acoustic wave source to contact a portion of an outer envelope of the acoustically propagative medium at the emission region, in an orientation to emit the acoustic waves to propagate through the acoustically propagative medium, from the emission region toward the reception region, in a propagation direction parallel to an emission axis; and
arranging a linear array of individual acoustic sensors, the linear array including the plurality of individual acoustic sensors, such that an orientation axis of the linear array is perpendicular to the emission axis and the individual acoustic sensors of the linear array are in contact with a portion of the outer envelope of the acoustically propagative medium at the reception region, and the individual acoustic sensors of the array face parallel to an alignment axis that is perpendicular to the orientation axis and opposite the direction of the emitted acoustic waves propagation,
wherein
the calculation instructions stored in the data recording medium connected to the programmable electronic calculator are configured to cause the programmable electronic calculator to perform the calculating the acoustic field values along a geometrical plane that is parallel to the alignment axis and to the orientation axis, in accordance with the reconstruction algorithm.

10. An apparatus for imaging in real time the propagation of acoustic waves, including any infrasound to ultrasound acoustic waves, in an acoustically propagative medium, comprising:
an acoustic wave source structured to contact an envelope of the acoustically propagative medium at an emission region and including an acoustic wave source configured to emit acoustic waves, while in the contact, in directions that include a direction toward a reception region of the acoustically propagative medium, the reception region being distinct from the emission region;
a plurality of individual acoustic sensors, structured to contact a plurality of locations on an envelope of the acoustically propagative medium, at the reception region, and structured to:
generate, over a detection interval, voltage signal waveform values indicative of the emitted acoustic waves as received, and
perform a succession of simultaneous acquisitions of the voltage signal waveform values, at instants of time in a succession of instants of time within a detection interval, and output a corresponding succession of simultaneously acquired voltage signal waveform values
an acoustic scanner, connected to the plurality of individual acoustic sensors, comprising:
at least one programmable electronic calculator connected to at least one data recording medium and, stored in the at least one data recording medium, executable acoustic field value calculation instructions and executable digital pixel image generating instructions, wherein the executable acoustic field value calculation instructions, when executed, cause the at least one programmable electronic calculator to calculate a group of acoustic field values that represent an image of an acoustic beam of the emitted acoustic waves at a plurality of positions in a region in the acoustically propagative medium between the emission region and the reception region, based on the succession of simultaneously acquired voltage signal waveform values and in accordance with a reconstruction algorithm, the executable acoustic digital pixel image generating instructions, when executed, cause the at least one programmable electronic calculator to generate a digital pixel image based at least in part on the group of acoustic field values; and a display, connected to the acoustic scanner, and configure to display the digital pixel image.

11. The apparatus of claim 10, wherein the acoustic sensors are configured to be located opposite to the emission region, in a sensor array that faces toward the acoustic wave source.

12. The apparatus of claim 10, wherein
the individual acoustic sensors are acoustic sensors in a two-dimensional matrix of acoustic sensors, which a plurality of adjacent sensor arrays, each comprising a linear array of individual sensors arranged along mutually parallel orientation axes, and
the calculating is configured to generate the acoustic field values to represent a three-dimensional image of the acoustic beam.

13. The apparatus of claim 10, wherein the acoustic wave source is an ultrasound wave source, the individual acoustic sensors are ultrasound sensors, and the emitted acoustic waves are ultrasounds waves, having respective wave frequencies between 100 kHz and 150 MHz.

14. A method for imaging in real time the propagation of a mechanical wave in an acoustically propagative medium, comprising the steps consisting of:

A) emitting, by an acoustic wave source, mechanical waves at an emission region of the acoustically propagative medium, to propagate in a propagation direction toward a reception region of the acoustically propagative medium, the reception region being distinct from the emission region;

B) measuring, by a plurality of acoustic sensors placed at the reception region, voltage signal waveform values indicative of the acoustic waves as received at a plurality of locations in the reception region of the acoustically propagative medium;

C) successive simultaneous acquisitions, by an acoustic scanner connected to the plurality of acoustic sensors, of the voltage signal waveform values, at instants of time in a succession of instants of time within a detection interval that is delayed relative to the emitting acoustic waves;

D) calculating, by a programmable electronic calculator that is connected to an acoustic scanner, based on the successive simultaneous acquisitions of the voltage signal waveform values and in accordance with a reconstruction algorithm, acoustic field values that represent an image of an acoustic beam of the emitted mechanical waves, at a region in plurality of positions in the acoustically propagative medium between the emission region and the reception region;

E) generating, by the programmable electronic calculator or by another programmable electronic calculator connected to the acoustic scanner, a digital pixel image, based on the acoustic field values; and F) displaying, on a display connected to the acoustic scanner, the digital pixel image.

15. The method of claim 14, further comprising repeating a sequence of steps A) through D), wherein, in each repeat:
the step C) successive simultaneous acquisitions of the voltage signal waveform values are at instants of time in a succession of instants of time within another detection interval.

16. The method of claim 2, wherein the plurality of acoustic sensors are in a sensor array, the sensor array comprising a plurality of switchable sub-groups of sensors, comprising switchable mode acoustic transducers, wherein:
step b) further comprises a sub-group of the plurality of switchable sub-groups of acoustic sensors performing the succession of simultaneous acquisitions over a detection interval that starts at a time instant and has a detection duration,
the method comprising repeating steps a), b) and c) for each given sub-group of sensors of the plurality of sub-groups of sensors,
the step b) comprising the given sub-group of the plurality of switchable sub-groups of acoustic sensors performing the succession of simultaneous acquisitions at each repetition,
the step c) comprising calculating by the programmable electronic calculator a group of acoustic field values that represent an image of an acoustic beam relative to the given sub-group of sensors,
and wherein step d) comprises generating a digital pixel image based on the groups of acoustic field values that represent an image of an acoustic beam relative to each sub-group of sensors of the plurality of switchable sub-groups of sensors.

17. The apparatus of claim 10, further comprising a programmable timing controller, connected to the acoustic wave source and configured to detect a beginning of the emitting and, in response, generate a trigger signal, the programmable timing controller including a processor and connected to the processor a recording medium that stores executable emission detection and trigger generating instructions that cause the processor to detect the beginning of the emitting and, in response, to generate the trigger signal.

18. The method of claim 1, wherein the reception region is located at a position corresponding to the propagation of the acoustic beam, such that a significant proportion of an acoustic power emitted by the acoustic wave source is collected by a measurement surface of the individual acoustic sensors.

19. The method of claim 16, wherein the acoustic wave source is configured to emit according to an emission axis, the emission axis being a symmetry axis of the acoustic beam, the reception region being located opposition to the emission region according to the emission axis.

20. The method of claim 1, further comprising generating, by the programmable electronic calculator or by another programmable electronic calculator connected to the acoustic scanner, a digital pixel image of an envelope of the acoustic beam, based at least in part on the group of acoustic field values, the generating comprising the programmable electronic calculator or the other programmable electronic calculator executing executable image generating instructions stored in the data recording medium, or in another data recording medium connected to the other programmable electronic calculator.

* * * * *